US008784735B2

(12) United States Patent
Winther et al.

(10) Patent No.: US 8,784,735 B2
(45) Date of Patent: *Jul. 22, 2014

(54) APPARATUS FOR AUTOMATED PROCESSING BIOLOGICAL SAMPLES

(71) Applicants: Lars Winther, Smoerum (DK); Marc Key, Ojai, CA (US); Kristopher Buchanan, Fort Collins, CO (US); John Favuzzi, Santa Barbara, CA (US); Benno Guggenheimer, Denver, CO (US)

(72) Inventors: Lars Winther, Smoerum (DK); Marc Key, Ojai, CA (US); Kristopher Buchanan, Fort Collins, CO (US); John Favuzzi, Santa Barbara, CA (US); Benno Guggenheimer, Denver, CO (US)

(73) Assignee: Dako Denmark A/S (DK)

( * ) Notice: Subject to any disclaimer, the term of this patent is extended or adjusted under 35 U.S.C. 154(b) by 0 days.

This patent is subject to a terminal disclaimer.

(21) Appl. No.: 13/964,562

(22) Filed: Aug. 12, 2013

(65) Prior Publication Data

US 2013/0330252 A1 Dec. 12, 2013

Related U.S. Application Data

(60) Continuation of application No. 13/493,969, filed on Jun. 11, 2012, now Pat. No. 8,529,836, which is a division of application No. 10/539,308, filed as application No. PCT/US03/40520 on Dec. 19, 2003, now Pat. No. 8,216,512.

(60) Provisional application No. 60/435,601, filed on Dec. 20, 2002.

(51) Int. Cl.
*G01N 35/00* (2006.01)

(52) U.S. Cl.
USPC .............. 422/67; 422/68.1; 422/65; 422/292; 422/297; 422/302; 435/40.5; 436/46; 436/47

(58) Field of Classification Search
USPC ............ 422/68.1, 65, 67, 292, 297, 300, 302; 435/40.5; 436/46, 47
See application file for complete search history.

(56) References Cited

U.S. PATENT DOCUMENTS 3,219,416 A 11/1965 Natelson
3,398,935 A 8/1968 Livesey et al.
(Continued)

FOREIGN PATENT DOCUMENTS

AU 0644876 B2 12/1993
CA 2172363 3/1995
(Continued)

OTHER PUBLICATIONS

U.S. Appl. No. 60/435,601, "Sample Processing System and Methods of Sample Processing," filed Dec. 20, 2002, 81 pages.
(Continued)

*Primary Examiner* — Shogo Sasaki
(74) *Attorney, Agent, or Firm* — Finnegan, Henderson, Farabow, Garrett & Dunner LLP (57) ABSTRACT

The present invention concerns an apparatus for automatic processing at least one biological sample accommodated on a carrier member, such as a slide by applying a predetermined amount of reagents in a predetermined sequence according to a processing protocol, said apparatus comprising; a housing frame; at least one processing section for accommodating at least one slide, the at least one processing section is provided within the housing; a hood cover protecting the at least one processing section in said housing; wherein the hood cover completely encloses the processing section defining an interior space; and wherein the apparatus further comprises climate control device provided to control the environment within the interior space.

32 Claims, 4 Drawing Sheets

(56) References Cited

U.S. PATENT DOCUMENTS

| | | | |
|---|---|---|---|
| 3,482,082 | A | 12/1969 | J. Isreeli |
| 3,513,320 | A | 5/1970 | R.J. Weldon |
| 3,553,438 | A | 1/1971 | Blitz et al. |
| 3,547,064 | A | 4/1971 | Binnings et al. |
| 3,600,900 | A | 8/1971 | Buddecke |
| 3,644,715 | A | 2/1972 | Holderith |
| 3,660,638 | A | 5/1972 | Oberli |
| 3,680,967 | A | 8/1972 | Englehardt |
| 3,772,154 | A | 11/1973 | Isenberg et al. |
| 3,801,775 | A | 4/1974 | Acker |
| 3,807,851 | A | 4/1974 | Knox et al. |
| 3,831,006 | A | 8/1974 | Chaffin, Iii et al. |
| 3,851,972 | A | 12/1974 | Smith et al. |
| 3,853,092 | A | 12/1974 | Amos et al. |
| 3,854,703 | A | 12/1974 | Gibbs et al. |
| 3,873,079 | A | 3/1975 | Kuus |
| 3,876,297 | A | 4/1975 | Appeldorn et al. |
| 3,909,203 | A | 9/1975 | Young et al. |
| RE28,585 | E | 10/1975 | Amos et al. |
| 3,916,157 | A | 10/1975 | Roulette et al. |
| 3,916,160 | A | 10/1975 | Russo et al. |
| 3,971,917 | A | 7/1976 | Maddox et al. |
| 3,976,028 | A | 8/1976 | Howells et al. |
| 3,994,594 | A | 11/1976 | Sandrock et al. |
| 4,013,038 | A | 3/1977 | Rogers et al. |
| 4,018,565 | A | 4/1977 | Fletcher, III et al. |
| 4,039,288 | A | 8/1977 | Moran |
| 4,066,412 | A | 1/1978 | Johnson et al. |
| 4,083,638 | A | 4/1978 | Sandrock et al. |
| 4,084,541 | A | 4/1978 | Ito |
| 4,092,952 | A | 6/1978 | Wilkie et al. |
| 4,100,309 | A | 7/1978 | Micklus et al. |
| 4,113,437 | A | 9/1978 | Duff et al. |
| 4,115,861 | A | 9/1978 | Allington |
| 4,133,642 | A | 1/1979 | Nosaka |
| 4,135,883 | A | 1/1979 | McNeil et al. |
| 4,159,875 | A | 7/1979 | Hauser |
| 4,163,643 | A | 8/1979 | Hunter et al. |
| 4,200,056 | A | 4/1980 | Johnson |
| 4,200,607 | A | 4/1980 | Suzuki |
| 4,227,810 | A | 10/1980 | Sandrock et al. |
| 4,245,967 | A | 1/1981 | Busselet |
| 4,263,504 | A | 4/1981 | Thomas |
| 4,281,387 | A | 7/1981 | Kraft et al. |
| 4,286,146 | A | 8/1981 | Uno et al. |
| RE30,730 | E | 9/1981 | Duff |
| 4,298,571 | A | 11/1981 | DiFulvio et al. |
| 4,311,667 | A | 1/1982 | Gocho |
| 4,323,537 | A | 4/1982 | Mody |
| 4,338,279 | A | 7/1982 | Orimo et al. |
| 4,346,056 | A | 8/1982 | Sakurada |
| 4,371,498 | A | 2/1983 | Scordato et al. |
| 4,404,641 | A | 9/1983 | Bazarnik |
| 4,406,547 | A | 9/1983 | Aihara |
| 4,447,395 | A | 5/1984 | Englar et al. |
| 4,455,280 | A | 6/1984 | Shinohara et al. |
| 4,467,073 | A | 8/1984 | Creasy |
| 4,467,603 | A | 8/1984 | Wilson |
| 4,488,679 | A | 12/1984 | Bockholt et al. |
| 4,510,169 | A | 4/1985 | Linner |
| 4,517,160 | A | 5/1985 | Galle et al. |
| 4,528,159 | A | 7/1985 | Liston |
| 4,531,455 | A | 7/1985 | Palmer |
| 4,539,632 | A | 9/1985 | Hansen et al. |
| 4,558,946 | A | 12/1985 | Galle et al. |
| 4,567,748 | A | 2/1986 | Klass et al. |
| 4,571,699 | A | 2/1986 | Herzog et al. |
| 4,585,622 | A | 4/1986 | Bowe et al. |
| 4,609,017 | A | 9/1986 | Coulter et al. |
| 4,624,588 | A | 11/1986 | Bivin |
| 4,634,576 | A | 1/1987 | Galle et al. |
| 4,634,850 | A | 1/1987 | Pierce et al. |
| 4,643,879 | A | 2/1987 | Hanaway |
| 4,647,432 | A | 3/1987 | Wakatake |
| 4,647,543 | A | 3/1987 | Stöcker |
| 4,656,006 | A | 4/1987 | Assmann et al. |
| 4,664,526 | A | 5/1987 | Scheffler et al. |
| 4,675,299 | A | 6/1987 | Witty et al. |
| 4,678,752 | A | 7/1987 | Thorne et al. |
| 4,678,894 | A | 7/1987 | Shafer |
| 4,681,741 | A | 7/1987 | Hanaway |
| 4,683,120 | A | 7/1987 | Meserol et al. |
| 4,692,308 | A | 9/1987 | Riley et al. |
| 4,692,603 | A | 9/1987 | Brass et al. |
| 4,695,430 | A | 9/1987 | Coville et al. |
| 4,708,886 | A | 11/1987 | Nelson |
| 4,719,087 | A | 1/1988 | Hanaway |
| 4,727,033 | A | 2/1988 | Hijikata et al. |
| 4,728,783 | A | 3/1988 | Brass et al. |
| 4,728,959 | A | 3/1988 | Maloney et al. |
| 4,729,661 | A | 3/1988 | Bell |
| 4,738,824 | A | 4/1988 | Takeuchi |
| 4,751,186 | A | 6/1988 | Baisch et al. |
| 4,754,127 | A | 6/1988 | Brass et al. |
| 4,754,414 | A | 6/1988 | Gocho |
| 4,764,342 | A | 8/1988 | Kelln et al. |
| 4,774,055 | A | 9/1988 | Wakatake et al. |
| 4,781,891 | A | 11/1988 | Galle et al. |
| 4,782,221 | A | 11/1988 | Brass et al. |
| 4,794,239 | A | 12/1988 | Allais |
| 4,795,613 | A | 1/1989 | Azuma et al. |
| 4,795,710 | A | 1/1989 | Muszak et al. |
| 4,797,938 | A | 1/1989 | Will |
| 4,800,762 | A | 1/1989 | Sugaya |
| 4,808,380 | A | 2/1989 | Minekane |
| 4,815,978 | A | 3/1989 | Mazza et al. |
| 4,817,916 | A | 4/1989 | Rawstron |
| 4,824,641 | A | 4/1989 | Williams |
| 4,844,887 | A | 7/1989 | Galle et al. |
| 4,847,208 | A | 7/1989 | Bogen |
| 4,849,177 | A | 7/1989 | Jordan |
| 4,855,109 | A | 8/1989 | Muraishi et al. |
| 4,855,110 | A | 8/1989 | Marker et al. |
| 4,865,811 | A | 9/1989 | Newton et al. |
| 4,868,129 | A | 9/1989 | Gibbons et al. |
| 4,869,114 | A | 9/1989 | Kido et al. |
| 4,871,682 | A | 10/1989 | Mazza |
| 4,873,877 | A | 10/1989 | Harris |
| 4,874,936 | A | 10/1989 | Chandler et al. |
| 4,886,590 | A | 12/1989 | Tittle |
| 4,896,029 | A | 1/1990 | Chandler et al. |
| 4,900,513 | A | 2/1990 | Barker et al. |
| 4,919,887 | A | 4/1990 | Wakatake |
| 4,924,078 | A | 5/1990 | Sant'Anselmo et al. |
| 4,933,147 | A | 6/1990 | Hollar et al. |
| 4,935,875 | A | 6/1990 | Shah et al. |
| 4,939,354 | A | 7/1990 | Priddy et al. |
| 4,939,674 | A | 7/1990 | Price et al. |
| 4,943,415 | A | 7/1990 | Przybylowicz et al. |
| 4,961,906 | A | 10/1990 | Andersen et al. |
| 4,965,049 | A | 10/1990 | Lillig et al. |
| 4,967,606 | A | 11/1990 | Wells et al. |
| 4,985,206 | A | 1/1991 | Bowman et al. |
| 4,986,891 | A | 1/1991 | Sarrine et al. |
| 4,988,482 | A | 1/1991 | Weston |
| 4,998,010 | A | 3/1991 | Chandler et al. |
| 5,031,797 | A | 7/1991 | Boris et al. |
| 5,051,238 | A | 9/1991 | Umetsu et al. |
| 5,053,609 | A | 10/1991 | Priddy et al. |
| 5,059,393 | A | 10/1991 | Quenin et al. |
| 5,068,091 | A | 11/1991 | Toya |
| 5,073,504 | A | 12/1991 | Bogen |
| 5,075,079 | A | 12/1991 | Kerr et al. |
| 5,081,038 | A | 1/1992 | Sugaya et al. |
| 5,102,624 | A | 4/1992 | Muraishi |
| 5,104,527 | A | 4/1992 | Clinkenbeard |
| 5,106,583 | A | 4/1992 | Raysberg et al. |
| 5,118,369 | A | 6/1992 | Shamir |
| 5,122,342 | A | 6/1992 | McCullochh et al. |
| 5,124,536 | A | 6/1992 | Priddy et al. |
| 5,180,606 | A | 1/1993 | Stokes et al. |
| 5,202,552 | A | 4/1993 | Little et al. |
| 5,225,325 | A | 7/1993 | Miller et al. |
| 5,229,074 | A | 7/1993 | Heath et al. |

(56) References Cited

U.S. PATENT DOCUMENTS

| | | |
|---|---|---|
| 5,232,664 A | 8/1993 | Krawzak et al. |
| 5,250,262 A | 10/1993 | Heidt et al. |
| 5,281,395 A | 1/1994 | Markart et al. |
| 5,282,149 A | 1/1994 | Grandone et al. |
| 5,289,385 A | 2/1994 | Grandone |
| 5,311,426 A | 5/1994 | Donohue et al. |
| 5,316,319 A | 5/1994 | Suggs |
| 5,316,452 A | 5/1994 | Bogen et al. |
| 5,316,726 A | 5/1994 | Babson et al. |
| 5,316,728 A | 5/1994 | Hayashi et al. |
| 5,322,771 A | 6/1994 | Rybski et al. |
| 5,331,176 A | 7/1994 | Sant' Anselmo et al. |
| 5,338,358 A | 8/1994 | Mizusawa et al. |
| 5,346,672 A | 9/1994 | Stapleton et al. |
| 5,350,697 A | 9/1994 | Swope et al. |
| 5,355,304 A | 10/1994 | DeMoranville et al. |
| 5,355,439 A | 10/1994 | Bernstein et al. |
| 5,355,695 A | 10/1994 | Kawaguchi et al. |
| 5,356,595 A | 10/1994 | Kanamori et al. |
| 5,365,614 A | 11/1994 | Perkins |
| 5,366,896 A | 11/1994 | Margrey et al. |
| 5,369,261 A | 11/1994 | Shamir |
| 5,380,486 A | 1/1995 | Anami |
| 5,382,511 A | 1/1995 | Stapleton |
| 5,395,588 A | 3/1995 | North, Jr. et al. |
| 5,399,316 A | 3/1995 | Yamada |
| 5,417,213 A | 5/1995 | Prince |
| 5,418,138 A | 5/1995 | Miller et al. |
| 5,424,036 A | 6/1995 | Ushikubo |
| 5,425,918 A | 6/1995 | Healey et al. |
| 5,428,740 A | 6/1995 | Wood et al. |
| 5,431,455 A | 7/1995 | Seely |
| 5,432,056 A | 7/1995 | Hartman et al. |
| 5,439,645 A | 8/1995 | Saralegui et al. |
| 5,439,649 A | 8/1995 | Tseung et al. |
| 5,439,826 A | 8/1995 | Kontorovich |
| 5,446,652 A | 8/1995 | Peterson et al. |
| 5,449,622 A | 9/1995 | Yabe et al. |
| 5,473,551 A | 12/1995 | Sato et al. |
| 5,487,975 A | 1/1996 | Miller et al. |
| 5,544,650 A | 8/1996 | Boon et al. |
| 5,549,848 A | 8/1996 | Zeheb et al. |
| 5,552,087 A | 9/1996 | Zeheb et al. |
| 5,573,727 A | 11/1996 | Keefe |
| 5,578,452 A | 11/1996 | Shi et al. |
| 5,595,707 A | 1/1997 | Copeland et al. |
| 5,602,674 A | 2/1997 | Weissman et al. |
| 5,612,524 A | 3/1997 | Sant' Anselmo et al. |
| 5,645,114 A | 7/1997 | Bogen et al. |
| 5,646,046 A | 7/1997 | Fischer et al. |
| 5,646,049 A | 7/1997 | Tayi |
| 5,649,537 A | 7/1997 | Anelli et al. |
| 5,650,136 A | 7/1997 | Platzek et al. |
| 5,650,327 A | 7/1997 | Copeland et al. |
| 5,654,199 A | 8/1997 | Copeland et al. |
| 5,654,200 A | 8/1997 | Copeland et al. |
| 5,656,493 A | 8/1997 | Mullis et al. |
| 5,675,715 A | 10/1997 | Bernstein et al. |
| 5,677,966 A | 10/1997 | Doerrer et al. |
| 5,681,543 A | 10/1997 | Schmitt-Willich et al. |
| 5,695,739 A | 12/1997 | Schmitt-Willich et al. |
| 5,696,887 A | 12/1997 | Bernstein et al. |
| 5,723,092 A | 3/1998 | Babson |
| 5,733,528 A | 3/1998 | Felder et al. |
| 5,737,449 A | 4/1998 | Lee |
| 5,737,499 A | 4/1998 | Bernstein et al. |
| 5,758,033 A | 5/1998 | Bernstein et al. |
| 5,776,414 A | 7/1998 | Itani et al. |
| 5,798,092 A | 8/1998 | Schmitt-Willich et al. |
| 5,820,849 A | 10/1998 | Schmitt-Willich et al. |
| 5,839,091 A | 11/1998 | Rhett et al. |
| 5,854,075 A | 12/1998 | Levine et al. |
| 5,875,286 A | 2/1999 | Bernstein et al. |
| 5,876,698 A | 3/1999 | Schmitt-Willich et al. |
| 5,885,529 A | 3/1999 | Babson et al. |
| 5,888,576 A | 3/1999 | Nagano |
| 5,888,733 A | 3/1999 | Hyldig-Nielsen et al. |
| 5,888,876 A | 3/1999 | Shiozawa et al. |
| 5,896,488 A | 4/1999 | Jeong |
| 5,930,461 A | 7/1999 | Bernstein et al. |
| 5,945,341 A | 8/1999 | Howard, III |
| 5,947,167 A | 9/1999 | Bogen et al. |
| 5,948,359 A | 9/1999 | Kalra et al. |
| 5,958,341 A | 9/1999 | Chu |
| 5,963,368 A | 10/1999 | Domanik et al. |
| 5,965,454 A | 10/1999 | Farmilo et al. |
| 5,985,563 A | 11/1999 | Hyldig-Nielsen et al. |
| 5,994,071 A | 11/1999 | Ross et al. |
| 6,017,495 A | 1/2000 | Ljungmann |
| 6,019,945 A | 2/2000 | Ohishi et al. |
| 6,045,759 A | 4/2000 | Ford et al. |
| 6,080,363 A | 6/2000 | Takahashi et al. |
| 6,083,490 A | 7/2000 | Ellis et al. |
| 6,092,695 A | 7/2000 | Loeffler |
| 6,093,574 A | 7/2000 | Druyor-Sanchez et al. |
| 6,096,271 A | 8/2000 | Bogen et al. |
| 6,097,995 A | 8/2000 | Tipton et al. |
| 6,104,483 A | 8/2000 | Sebok et al. |
| 6,110,425 A | 8/2000 | Gao et al. |
| 6,110,676 A | 8/2000 | Coull et al. |
| 6,142,292 A | 11/2000 | Patterson |
| 6,169,169 B1 | 1/2001 | Hyldig-Nielsen et al. |
| 6,180,061 B1 | 1/2001 | Bogen et al. |
| 6,183,693 B1 | 2/2001 | Bogen et al. |
| 6,192,945 B1 | 2/2001 | Ford et al. |
| 6,193,933 B1 | 2/2001 | Sasaki et al. |
| 6,208,771 B1 | 3/2001 | Jared et al. |
| 6,235,476 B1 | 5/2001 | Bergmann et al. |
| 6,244,474 B1 | 6/2001 | Loeffler |
| 6,245,207 B1 | 6/2001 | Yasuda et al. |
| 6,248,590 B1 | 6/2001 | Malachowski |
| 6,281,004 B1 | 8/2001 | Bogen et al. |
| 6,287,772 B1 | 9/2001 | Stefano et al. |
| 6,296,809 B1 | 10/2001 | Richards et al. |
| 6,310,179 B1 | 10/2001 | Batz et al. |
| 6,327,395 B1 | 12/2001 | Hecht et al. |
| 6,335,208 B1 | 1/2002 | Lowry |
| 6,349,264 B1 | 2/2002 | Rhett et al. |
| 6,352,861 B1 | 3/2002 | Copeland et al. |
| 6,358,682 B1 | 3/2002 | Jaffee et al. |
| 6,387,326 B1 | 5/2002 | Edwards et al. |
| 6,388,061 B1 | 5/2002 | Bergmann et al. |
| 6,395,562 B1 | 5/2002 | Hammock et al. |
| 6,403,036 B1 | 6/2002 | Rodgers et al. |
| 6,403,931 B1 | 6/2002 | Showalter et al. |
| 6,405,609 B1 | 6/2002 | Richards et al. |
| 6,408,931 B1 | 6/2002 | Tilak |
| 6,414,133 B1 | 7/2002 | Dietz-Band et al. |
| 6,416,713 B1 | 7/2002 | Ford et al. |
| 6,420,916 B1 | 7/2002 | Freeman |
| 6,426,794 B1 | 7/2002 | Trainoff |
| 6,444,170 B1 | 9/2002 | Heid et al. |
| 6,451,551 B1 | 9/2002 | Zhan et al. |
| 6,472,217 B1 | 10/2002 | Richards et al. |
| 6,495,106 B1 | 12/2002 | Kalra et al. |
| 6,498,037 B1 | 12/2002 | Carey et al. |
| 6,509,193 B1 | 1/2003 | Tajima |
| 6,534,008 B1 | 3/2003 | Angros |
| 6,537,818 B2 | 3/2003 | Reinhardt et al. |
| 6,541,261 B1 | 4/2003 | Bogen et al. |
| 6,544,798 B1 | 4/2003 | Christensen et al. |
| 6,548,822 B1 | 4/2003 | Morris et al. |
| 6,582,962 B1 | 6/2003 | Richards et al. |
| 6,594,537 B1 | 7/2003 | Bernstein et al. |
| 6,632,598 B1 | 10/2003 | Zhang et al. |
| 6,635,225 B1 | 10/2003 | Kaltenmeier et al. |
| 6,699,710 B1 | 3/2004 | Kononen et al. |
| 6,735,531 B2 | 5/2004 | Rhett et al. |
| 6,746,851 B1 | 6/2004 | Tseung et al. |
| 6,800,249 B2 | 10/2004 | de la torre-Bueno |
| 6,821,072 B2 | 11/2004 | Thiem et al. |
| 6,827,901 B2 | 12/2004 | Copeland et al. |
| 6,855,559 B1 | 2/2005 | Christensen et al. |
| 6,943,029 B2 | 9/2005 | Copeland et al. |

(56) References Cited

U.S. PATENT DOCUMENTS

| | | |
|---|---|---|
| 7,135,992 B2 | 11/2006 | Karlsson et al. |
| 7,142,852 B2 | 11/2006 | Tell et al. |
| 7,226,788 B2 | 6/2007 | De La Torre-Bueno |
| 7,303,725 B2 | 12/2007 | Reinhardt et al. |
| 7,378,055 B2 | 5/2008 | Lemme et al. |
| 7,396,508 B1 | 7/2008 | Richards et al. |
| 7,400,983 B2 | 7/2008 | Feingold et al. |
| 7,404,927 B2 | 7/2008 | Lemme et al. |
| 2001/0006417 A1 | 7/2001 | Modlin et al. |
| 2001/0010936 A1 | 8/2001 | Richards et al. |
| 2001/0037072 A1 | 11/2001 | Virtanen |
| 2001/0044124 A1 | 11/2001 | Bacus |
| 2001/0049114 A1 | 12/2001 | Bacus |
| 2001/0055799 A1 | 12/2001 | Baunoch et al. |
| 2002/0001849 A1 | 1/2002 | Copeland et al. |
| 2002/0009391 A1 | 1/2002 | Marquiss et al. |
| 2002/0019001 A1 | 2/2002 | Light |
| 2002/0072122 A1 | 6/2002 | Copeland et al. |
| 2002/0091593 A1 | 7/2002 | Fowler |
| 2002/0098595 A1 | 7/2002 | Lubman et al. |
| 2002/0110494 A1 | 8/2002 | Lemme et al. |
| 2002/0114733 A1 | 8/2002 | Copeland et al. |
| 2002/0116132 A1 | 8/2002 | Rhett et al. |
| 2002/0176801 A1 | 11/2002 | Giebeler et al. |
| 2002/0178547 A1 | 12/2002 | Shofner et al. |
| 2002/0182628 A1 | 12/2002 | Dietz-Band et al. |
| 2003/0003537 A1 | 1/2003 | Fischer et al. |
| 2003/0022391 A1 | 1/2003 | Richards et al. |
| 2003/0032048 A1 | 2/2003 | Kim et al. |
| 2003/0043963 A1 | 3/2003 | Yamagami et al. |
| 2003/0059790 A1 | 3/2003 | Jaffee et al. |
| 2003/0087443 A1 | 5/2003 | Pressman et al. |
| 2003/0099573 A1 | 5/2003 | Tseung et al. |
| 2003/0100043 A1 | 5/2003 | Kalra et al. |
| 2003/0119200 A1 | 6/2003 | Taft et al. |
| 2003/0120633 A1 | 6/2003 | Torre-Bueno |
| 2003/0124729 A1 | 7/2003 | Christensen et al. |
| 2003/0162221 A1 | 8/2003 | Bader et al. |
| 2003/0200111 A1 | 10/2003 | Damji |
| 2003/0215357 A1 | 11/2003 | Malterer et al. |
| 2004/0002163 A1 | 1/2004 | Reinhardt et al. |
| 2004/0033163 A1 | 2/2004 | Tseung et al. |
| 2004/0219069 A1 | 11/2004 | Kalra et al. |
| 2004/0265185 A1 | 12/2004 | Kitagawa |
| 2004/0266015 A1 | 12/2004 | Favuzzi et al. |
| 2005/0038676 A1 | 2/2005 | Showalter et al. |
| 2005/0064535 A1 | 3/2005 | Favuzzi et al. |
| 2005/0124028 A1 | 6/2005 | Windeyer et al. |
| 2005/0159982 A1 | 7/2005 | Showalter et al. |
| 2006/0045806 A1 | 3/2006 | Winther et al. |
| 2006/0046298 A1 | 3/2006 | Key et al. |
| 2006/0063265 A1 | 3/2006 | Welcher et al. |
| 2006/0085140 A1 | 4/2006 | Feingold et al. |
| 2006/0088928 A1 | 4/2006 | Sweet et al. |
| 2006/0088940 A1 | 4/2006 | Feingold et al. |
| 2006/0105359 A1 | 5/2006 | Favuzzi et al. |
| 2006/0148063 A1 | 7/2006 | Fauzzi et al. |
| 2006/0172426 A1 | 8/2006 | Buchanan et al. |
| 2006/0265133 A1 | 11/2006 | Cocks et al. |
| 2007/0010912 A1 | 1/2007 | Feingold et al. |
| 2007/0196909 A1 | 8/2007 | Showalter et al. |

FOREIGN PATENT DOCUMENTS

| | | |
|---|---|---|
| DE | 4313807 | 11/1993 |
| DE | 69417908 T2 | 11/1999 |
| EP | 0285851 A2 | 10/1988 |
| EP | 0290018 A2 | 11/1988 |
| EP | 0310303 A1 | 4/1989 |
| EP | 0325101 A1 | 7/1989 |
| EP | 0600939 B1 | 6/1994 |
| EP | 0722363 B1 | 7/1996 |
| EP | 0881481 A1 | 12/1998 |
| ES | 2160486 A1 | 11/2001 |
| FR | 2239167 | 7/1973 |
| GB | 2216259 | 3/1988 |
| GB | 2218514 A | 3/2003 |
| JP | 54014287 A | 2/1979 |
| JP | 55107957 | 8/1980 |
| JP | 63240688 A2 | 10/1988 |
| JP | 03209163 A2 | 12/1991 |
| WO | WO 85/03571 | 8/1985 |
| WO | WO 86/02163 | 4/1986 |
| WO | WO 87/00086 | 1/1987 |
| WO | WO 87/00280 | 1/1987 |
| WO | WO 87/06695 | 11/1987 |
| WO | WO 88/02866 | 4/1988 |
| WO | WO 8802865 | 4/1988 |
| WO | WO 89/01616 | 2/1989 |
| WO | WO 91/13335 | 9/1991 |
| WO | WO 92/01919 A1 | 2/1992 |
| WO | WO 93/03451 A1 | 2/1993 |
| WO | WO 93/20440 | 10/1993 |
| WO | WO 94/06080 | 3/1994 |
| WO | WO 95/10035 | 4/1995 |
| WO | WO 95/10035 A2 | 4/1995 |
| WO | WO 95/10035 A3 | 4/1995 |
| WO | WO 95/28179 | 10/1995 |
| WO | WO 95/32741 | 12/1995 |
| WO | WO 95/33240 | 12/1995 |
| WO | WO 97/23732 A1 | 7/1997 |
| WO | WO 97/26541 | 7/1997 |
| WO | WO 97/26541 A1 | 7/1997 |
| WO | WO 99/34190 A1 | 7/1999 |
| WO | WO 99/43434 | 9/1999 |
| WO | WO 99/44031 | 9/1999 |
| WO | WO 99/49295 A1 | 9/1999 |
| WO | WO 99/55916 A1 | 11/1999 |
| WO | WO 99/57309 A1 | 11/1999 |
| WO | WO 00/02030 A1 | 1/2000 |
| WO | WO 00/02660 | 1/2000 |
| WO | WO 00/02660 A1 | 1/2000 |
| WO | WO 00/36393 A2 | 6/2000 |
| WO | WO 01/02859 A1 | 1/2001 |
| WO | WO 01/02861 A1 | 1/2001 |
| WO | WO 0106255 A | 1/2001 |
| WO | WO 01/07890 A2 | 2/2001 |
| WO | WO 01/51909 | 7/2001 |
| WO | WO 01/51909 A1 | 7/2001 |
| WO | WO 01/55346 A3 | 8/2001 |
| WO | WO 01/68259 | 9/2001 |
| WO | WO 01/68269 A1 | 9/2001 |
| WO | WO 01/87487 A2 | 11/2001 |
| WO | WO 01/87487 A3 | 11/2001 |
| WO | WO 01/88500 | 11/2001 |
| WO | WO 02/056121 | 7/2002 |
| WO | WO 02/064812 | 8/2002 |
| WO | WO 03/045560 | 6/2003 |
| WO | WO 03/045560 A2 | 6/2003 |
| WO | WO 03/045560 A3 | 6/2003 |
| WO | WO 03/052386 | 6/2003 |
| WO | WO 03/052386 A1 | 6/2003 |
| WO | WO 2004/057307 A1 | 7/2004 |
| WO | WO 2004/057308 A1 | 7/2004 |
| WO | WO 2004/058404 A2 | 7/2004 |
| WO | WO 2004/058404 A3 | 7/2004 |
| WO | WO 2004/058950 A1 | 7/2004 |
| WO | WO 2004/059284 A2 | 7/2004 |
| WO | WO 2004/059284 A3 | 7/2004 |
| WO | WO 2004/059287 A2 | 7/2004 |
| WO | WO 2004/059287 A3 | 7/2004 |
| WO | WO 2004/059288 A2 | 7/2004 |
| WO | WO 2004/059288 A3 | 7/2004 |
| WO | WO 2004/059297 A1 | 7/2004 |
| WO | WO 2004/059441 | 7/2004 |
| WO | WO 2004/059441 A3 | 7/2004 |
| WO | WO 2004/074845 | 9/2004 |
| WO | WO 2004/074847 | 9/2004 |
| WO | WO 2005/031312 | 4/2005 |
| WO | WO 2005/084263 | 9/2005 |

OTHER PUBLICATIONS

European Patent Application No. 91 90 8695 Supplementary European Search Report, Search completed Mar. 26, 1993, 6 pages.

(56) References Cited

OTHER PUBLICATIONS

12 Most Frequently Asked Questions About Thermoelectric Cooling. In: Tellurex Corporation, accessed Oct. 27, 204, http://www.tellurex.com/12most.html, Oct. 27, 2004.
Chow et al, "Application of Existing Technology to Meet Increasing Demands for Automated Sample Handling," Clinical Chemistry, 36(9):1 579-1582. 1990.
Dricsoll et al., "Discreet Automated Chemistry System with Tableted Reagents," Clinical Chemistry, 29(9): 1609-1615, 1983.
Garza et al., "Bar Codes in the Clinical Laboratory," Clinical Laboratory Science, 4(1 ):23-24, Jan./Feb. 1991.
Innis et al., "DNA Sequencing with Themus Aquaticus DNA Polymerase and Direct Sequencing of Polymerase Chain-Amplified DNA," Proc. Natl. Acad. Sci, 85:9436-9440, Dec. 1988.
International Application No. PCTIUSO3I4O88O Written Opinion dated Sep. 28, 2005.
Lindeman et al., "Evaluation of the Automation of the Immunoenzymatic Procedures in a Routine Histo/Cytopathalogical Laboratory," Histopathology, 6:739-746, 1982.
Rappaport, "If Bar Code Works in Supermarkets, It Should Be Great for Medicine."PathologIst, 39(2): 39-40, 185, Feb. 1985.
Saiki et al., "Enzymatic Amplification of β-Globin Genomic Sequences and Restriction Site Analysis for Diagnosis of Sickle Cell Anemial," Science 230:1350-1353, Dec. 20, 1985.
Stark et al., An automated Devide of Immunocytochemistry, Journal of Immunological Methods, 1986, Elsevier, 107, pp. 89-92.
Tilzer et al., "Use of Bar Code Labels on Collection Tubes for Specimen Management in the Clinical Laboratory." Arch Pathol Lab Mcd, 112:1201-1202, Dec. 1988.
United States nonprovisional Application No. 071488,601, "Automated Biological Reaction Apparatus" filed Mar. 2, 1990.
United States nonprovisional Application No. 071924.052. "Automated Biological Reaction Apparatus" filed Aug. 31, 1992.
United States District Court, District of Arizona, *Ventana* v. *Cytologix*, CIV 02117 TUC (WDB) Defendant's Surreply in Opposition to Plaintiff's Motion for Preliminary Injunctive Relief filed Jul. 2002.
United States District Court, District of Arizona, *Ventana* v. *Cytologix*, CIV 02117 TUG (RCC) Plaintiff's Motion for Temporary Restraining Order filed Mar. 2002.
United States District Court, District of Arizona, *Ventana* v. *Cytologix*, CIV 02117 TUG (RCC) Plaintiff's Memorandum in Support of Petition for Temporary Restraining Order and Permanent Injunction filed Mar. 2002.
United States District Court, District of Arizona, *Ventana* v. *Cytologix*, CIV 02117 TUC (WDB) Ventana's Reply in Support of its Motion for Preliminary Relief filed Jun. 2002.
United States District Court, District of Arizona, CV03-92 TUC-RCC, *Ventana Medical* vs *Biogenix Laboratories*, Order and Opinion on Motion, Aug. 23, 2005.
United States District Court, District of Arizona, CV03-92 TUC-RCC, *Ventana Medical* vs *Biogenix* Laboratories Reporter's Transcript of Proceedings (Markman Hearing) before Honorable Raner C. Collins, Aug. 11, 2005.
United States District Court, District of Arizona, CV03-92 TUC-RCC. *Ventana Medical* vs *Biogenix Laboratories*, Order filed Oct. 4, 2005.
United States District Court, District of Arizona, CV03-92 TUC-RCC, *Ventana Medical* vs *Biogenix Laboratories*, Judgment in a CMI Case, Oct. 19, 2005.
United States District Court, District of Delaware, *Ventana* v. *Dakocytomation California*, CIV041522 (GMS) Order Construing the Terms of U.S. Patent No. 6,827901 dated Dec. 13, 2005.
United States District Court, Eastern District of Massachusetts, *Vision Biosystems (USA) Trading* v. *Ventana Medical Systems*, CIV 03CV10391GAO, Defendant's Statement of Undisputed Material Facts, in Support of its Cross-Motion for Summary Judgment of Infringement of the 861 Patent filed Jan. 2004.
United States District Court, Eastern District of Massachusetts, *Vision Biosystems (USA) Trading* v. *Ventana Medical Systems*, CIV 03CV103910A0, Defendant's Memorandum in Opposition to Plaintiff's Motion for Summary Judgment of No Infringement, and in Support of Defendant's Cross-Motion for Summary Judgment of Infringement of the 861 Patent, filed Jan. 15, 2004.
United States District Court, District of Massachusetts, *Vision Biosystems (USA) Trading* v. *Ventana Medical Systems*, CIV 03CVIO391GAO, Defendant's Statement of Material Facts in Dispute, in Opposition to Plaintiff's Motion for Summary Judgment o No Infringement of the 861 Patent, filed Jan. 15, 2004.
United States District Court, District of Massachusetts, *Vision Biosystems (USA) Trading* v. *Ventana Medical Systems*, CIV 03CV10391GAO, Memorandum and Order filed Sep. 30, 2004.
United States District Court, District of Massachusetts, *Vision Biosystems (USA) Trading* v. *Ventana Medical Systems*, CIV 03CV10391GAO, Plaintiff's motion for Summary Judgment of Non-Infringement Based on Collateral Estoppel filed Oct. 7, 2005.
United States District Court, District of Massachusetts, *Vision Biosystems (USA) Trading* v. *Ventana Medical Systems*, CIV 03CV10391GAO, Plaintiff's Statement of Undisputed Facts in Support of its Motion for Summary Judgment of Non-Infringement Based on Collateral Estoppel, filed Oct. 7, 2005.
United States District Court, District of Massachusetts, *Vision Biosystems (USA) Trading* v. *Ventana Medical Systems*, CIV 03CV10391GAO, Plaintiff's Memorandum in Support of its Motion for Summary Judgment of Non-Infringement Based on Collateral Estoppel, filed Oct. 7, 2005.
United States District Court. District of Massachusetts, *Vision Biosystems (USA) Trading* v. *Ventana Medical Systems*, CIV 03CV10391GAO, Declaration of Richard Wydeven in Support of Plaintiff's Motion for Summary Judgment of Non-Infringement Based on Collateral Estoppel, filed Oct. 7, 2005.
United States District Court. District of Massachusetts, *Vision Biosystems (USA) Trading* v. *Ventana Medical Systems*, CIV 03CV10391 GAO, Defendant Ventana Medical Systems, Inc.'s Memorandum in Opposition to Vision's Motion for Summary Judgment of Non-Infringement Based on Collateral Estoppel. filed Oct. 21, 2005.
United States District Court, District of Massachusetts, *Vision Biosystems (USA) Trading* v. *Ventana Medical Systems*, CIV 03CV10391 GAO, Defendant Ventena Medical Systems, Inc.'s Statement of Material Facts in Dispute, in Opposition to Vision's Motion for Summar Judgment of Non-Infringement Based on Collateral Estoppel, filed Oct. 21, 2005.
International Preliminary Examination Report, P142WO01, International Application No. PCT/US03/40519 filed Dec. 19, 2003.
International Preliminary Examination Report, P143WO01, International Application No. PCT/US03/40591 filed Dec. 19, 2003.
International Preliminary Examination Report, P131 WO01, International Application No. PCT/US03/40518 filed Dec. 19, 2003.
International Preliminary Examination Report, P139WO01, International Application No. PCT/US03/40880 filed Dec. 22, 2003.
International Preliminary Examination Report, P140WO01, International Application No. PCT/US03/00877 filed Dec. 15, 2003.
International Preliminary Examination Report, P144WO01, International Application No. PCT/US03/41022 filed Dec. 22, 2003.
International Preliminary Examination Report, P1 45W001, International Application No. PCT/US03/40520 filed Dec. 19, 2003, mailing date Mar. 27, 2006.
Written Opinion, P145WO01 • International Application No. PCT/US03/40520 filed Dec. 19, 2003.
International Preliminary Examination Report, P145WO01, International Application No. PCT/US03/40520 filed Dec. 19, 2003, mailing date May 31, 2005.
Written Opinion, P149WO01, International Application No. PCT/US03/40974 filed Dec. 19, 2003.
Written Opinion, International Application No. PCT/US03/40880 dated Sep. 28, 2005.
International Preliminary Examination Report. P1 49W001 • International Application No. PCT/US03/40974 filed Dec. 19, 2003.
U.S. Appl. No. 11/119,417, filed Apr. 30, 2005, Method and Apparatus for Pretreatment of Biological Samples.
Taylor, C., Creating a bar code chemistry system, Medical Laboratory Observer, Feb. 1993;25(2):34-6.

(56) References Cited

OTHER PUBLICATIONS

Singer, R. et al, Selection and evaluation of laboratory instrumentation in clinical chemistry: II Guidelines for selection and evaluation, Med Lab Sci. Jan. 1987;44(1):6-14.

Rocks, B. F. et at., Automatic analysers in clinical biochemistry, B F Rocks et al 1986 Clin. Phys. Physiol. Meas. 7 1-29.

Pearson, L. S., The use of bar coding technology, Medical Device Technology, Mar. 1994.

Lifshitz, M. 8, et al., Talking about Technology, Clinical Laboratory Management Review, Jan.-Feb. 1989;3 (1):53-4.

U.S. Appl. No. 60/487,998, An Interface Point Server, filed Jul. 17, 2003. 52 pages.

U.S. Appl. No. 10/054,535. Entitled Automated Biological Reaction Apparatus, now Patent No. 6.943,029 , Sep. 13, 2005.

Juroshek et al., A High-Power Automatic Network Analyzer for Measuring the RF Power Absorbed by Biological Samples in a TEM Cell, 1984, IEEE, gpo 818-824.

Meldrum et al., ACAPELLA, a capillary-based submicroliter automated sample preparation system for genome analysis, 1999, IEEE, p. 39-48.

Shepard, DNA purification robotics system, 1994, IEEE, gpo 424-425.

Suckau et al., Automation of MALDI-TOF Analysis for Proteomics, 1999, IEEE, p. 1-5.

Histologic, Technical Bulletin for Histotechnology, 2001, Internet, p. 21-44.

Garrett et al., Successful techniques for supporting multidisciplinary science programs with 'ROPOS: 1999, IEEE, p. 753-756.

Office Action dated Feb. 19, 2010 issued in U.S. Appl. No. 11/156,760, filed Jun. 20, 2005, Favuzzi et al.

Notice of Allowance dated Dec. 16, 2010 issued in U.S. Appl. No. 11/156,760, filed Jun. 20, 2005, Favuzzi et al.

APPARATUS FOR AUTOMATED PROCESSING BIOLOGICAL SAMPLES

This application is a continuation of application Ser. No. 13/493,969, filed Jun. 11, 2012, now U.S. Pat. No. 8,529,836, which is a divisional of application Ser. No. 10/539,308, filed Jun. 16, 2005, now U.S. Pat. No. 8,216,512, which is the United States National Stage of International Application No. PCT/US2003/040520, filed Dec. 19, 2003 which claims benefit under 35 U.S.C. 119(e) of U.S. Provisional Application No. 60/435,601, filed Dec. 20, 2002, each hereby incorporated by reference herein.

TECHNICAL FIELD

The present invention relates to a method and an apparatus for automatic processing of at least one biological sample accommodated on a carrier member, such as microscopic slide, by applying a predetermined amount of reagents in a sequence according to a processing protocol, wherein at least one slide is provided in a slide rack assembly.

This application relates to the field of sample processing systems and methods of processing samples. The present invention may be directed to the automated processing, treatment, or even staining of samples arranged on carriers, such as microscope slides, and in some embodiments, directed to the continuous or batch processing of samples and carriers, as well as washing elements of a sampling system. Embodiments may further relate to control systems for sample processing and data acquisition, data maintenance, and data retrieval for sample processing. Applications to which the present invention may especially relate include cytology, immunohistochemistry, in-situ hybridization, fluorescent in-situ hybridization, special staining, and microarrays, as well as potentially other chemical and biological applications.

BACKGROUND

The biological sample may suitably be selected from histological material, including formalin fixed and paraffin embedded material, cytological material, fine needle aspirates, cell smears, exfoliative cytological specimens, touch preparations, bone marrow specimens, sputum samples, expectorates, oral swabs, laryngeal swabs, vaginal swabs, bronchial aspirates, bronchial lavage, gastric lavage, and body fluids. Such may be subjected to various treatments.

Sample processing in immunohistochemical (IHC) applications and in other chemical and biological analyses may require one or a number of various processing sequences or protocols as part of an analysis of one or more samples. The sample processing sequences or protocols may be defined by the individual or organization requesting an analysis, such as a pathologist or histologist of a hospital, and may be further defined by the dictates of a particular analysis to be performed.

In preparation for sample analysis, a biological sample may be acquired by known sample acquisition techniques and may comprise, for example in IHC applications, tissues generally or even in some applications one or a plurality of isolated cells, such as in microarray samples, and may be presented on a sample carrier such as a microscope slide. Furthermore, the sample may be presented on the carrier variously and potentially in some form of preservation. As one example, a human biopsi sample may be fixed and embedded in a suitable media like paraffin or epon, before being mounted onto a carrier. The sample may be treated according to the protocol, which may include the following non limiting procedural steps: deparaffination, antigen retrieval, denaturing, washing, incubation with various immunological reagents, molecular probes or dyes, strigency wash or counterstaining.

Histological cytological, ISH, IHC special stains and other applications, for example, may require processing sequences or protocols that comprise many and laborious steps such as deparaffinization, target retrieval, and staining. Such steps are not special for ISH procedures, but goes for IHC, cytological, specials or ISH stainings. Previously, in some applications, these steps may have been performed manually, potentially creating a time-intensive protocol and necessitating personnel to be actively involved in the sample processing. Attempts have been made to automate sample processing to address the need for expedient sample processing and a less manually burdensome operation. However, such previous efforts may have not fully addressed the needs for an automated sample processing system. Previous efforts to automate sample processing may be deficient in several aspects that prevent more robust automated sample processing, such as: the lack of sufficient computer control and monitoring of sample processing; the lack of information sharing for processing protocol and processing status, especially for individual samples; the lack of diagnostic capabilities; and the lack of real-time or adaptive capabilities for multiple sample batch processing.

From U.S. Pat. No. 5,839,091 an automated sample processing for samples presented on carriers such as slides is known. In this apparatus, an array of slides is stained by a robotic device delivering reagents onto the slides. The staining apparatus is provided with a lid cover, which provides a protective cover of the biological samples on the carriers in the apparatus during the staining processes as well as containing stains of the some times hazardous reagent materials within the apparatus and preventing operators from being exposed to such stains.

Slides can be any suitable solid or semi solid support for the biological sample. In particular, the support may be a microscope slide, a membrane, a filter, a polymer slide, a chamber slide, a dish, or a petridish Some staining processes involve the use of hazardous materials, such as toxic materials. These materials may be collected in special containers in order to ensure safe handling of the waste material. However, this does not sufficiently protect the laboratory environment in which the apparatus is placed from being contaminated with toxic material. Moreover, in some staining processes or other treatments in the apparatus heat is applied. This increases the risk of vaporising reagents which then may escape to the outside of the apparatus.

In the apparatuses known in the art, a protective hood or similar plastic cover is put over the staining apparatus in order to shield off the biological samples during the staining. In this known technique, one risk is the drying out of slides and lack of control of airspeed and temperature.

DISCLOSURE OF INVENTION

On this background, it is an object of the invention to provide an apparatus for automatic staining of biological samples, in which the hazardous materials and toxic or otherwise damaging fumes are contained and automatically handled, so that operators need not be involved in the handling of such types of materials.

The invention consists of a method and an apparatus for automatic staining at least one biological sample accommodated on a carrier slide by applying a predetermined amount of reagents in a predetermined sequence according to a staining protocol, said apparatus comprising: a housing frame; at least one staining section for accommodating at least one slide, said at least one staining section is provided within said housing; a hood cover protecting said at least one staining section in said housing; wherein the hood cover completely encloses the staining section defining an interior space; and wherein the apparatus further comprises climate control device that provide control of the environment within said interior space; and sensor device to provide feedback signals to the climate control means.

In the staining apparatus, fumes from the reagents and other processing liquids used in the apparatus for performing the treatment of the biological samples are present. In an apparatus according to the invention, these fumes may be exhausted from the interior space of the apparatus, just as the climate in the apparatus may be controlled. In particular, in order to avoid the volatile fumes from escaping into the surroundings, the climate control device preferably includes a pressure control device that can ensure a slight sub-pressure within the interior space. By maintaining a slight sub-pressure inside the apparatus, the fumes are kept inside in the interior space, from where the climate control system may remove the volatile fumes. These fumes may advantageously be collected in suitable storage or otherwise be disposed of.

Advantageously, the climate control device may also include humidity control within the interior space. This makes an apparatus according to the invention more suitable for some special sample treatment applications, just as the climate requirement inside the laboratory where the apparatus is placed may be less strict. Moreover, the climate control device may preferably also include a temperature control device that can control the ambient temperature of the air within the interior space.

Climate control, especially control of temperature and humidity is important for ensuring standardized and reproducible staining protocols, as the biological samples can easily dry out or changes properties, including morphology and antigenicity. Also, the controlled environment can ensure uniform chemical reaction conditions on the slides during the staining protocol.

The climate control device in an apparatus according to the invention may include an exhaustion device that can remove fumes from the interior space. These exhaustion devices are preferably adapted to draw air from an outlet positioned below the level in which the at least one slide is accommodated. Hereby, fumes are drawn away from the hood and the slides. This may reduce any risk of cross-contamination. Cross contamination could be a problem, as some fumes can adsorb to the biological sample, resulting in a change of properties. Especially hydrophobic, acidic, basic, strong chaotropic or otherwise reactive or corrosive fumes can cause serious and unwanted cross contamination.

The sensor device is preferably adapted to sense at least one climate parameter from the group comprising temperature, pressure, humidity, airspeed and the presence of toxic elements in fume. These measured air characteristics are used for manipulating the inflowing air into the interior space, so that it is ensured that the biological samples are processed in a controlled ambient environment and that it is ensured that the samples do not dry out or are otherwise being deteriorated.

The sensor device may comprise internal sensors located inside the interior space. Alternatively, the sensor may comprise external sensors located outside the interior space, such as at or inside an air inlet/outlet manifold, in a laboratory facility accommodating the apparatus, or outside the building accommodating the laboratory.

In the preferred embodiment, the cover is at least one openable hood. The cover is an integrated part of the apparatus, e.g. a hinged hood which may be swung open. An automatic lock may be provided to prevent any opening during the processing.

In an embodiment, the cover is a plurality of covers arranged to cover a plurality of sections of the apparatus, such as at least one biological sample accommodated on a carrier in the at least one processing section. Hereby, different environments may be created for different samples. A plurality of interior spaces may be defined by a plurality of covers in the apparatus, each interior space including at least one section arranged for comprising at least one sample on a carrier and/or at least one section arranged for comprising at least one reagent in a container.

The climate control device may be arranged to controlling the climate in each interior space, comprising at least one sample on a carrier, according to a sample processing protocol defined for that particular sample. In an embodiment of the invention, the climate control device receives input signals from internal and/or external sensors, and are arranged to control the climate in each interior space, according to the input signals. The climate control device may then preferably connected for data communication with a data processing device, such as a computer, wherein the protocol for the processing of the particular sample is stored, and where from control data are provided to the climate control device. Hereby, an automatic climate control is provided for the sample processing, whereby it may be possible to provide a selected air environment for a particular sample processing protocol.

In a preferred embodiment of the invention, the hood cover is provided with one or more seal elements to provide an air-tight seal between the cover and the housing. Hereby, the sub-pressure need not be present or a higher pressure inside may be provided for achieving a more precise climate control inside the apparatus.

The exchange of air between the interior space and the surroundings may be carried out via an inlet and an outlet. In an embodiment of the invention, the inlet may be provided for supplying air into the interior space including an air inlet opening in the housing, and wherein air manipulation device are provided in addition to said inlet means to adapt the inflowing air with predetermined characteristics. Hereby, the inside climate of the air in the interior space may be accurately controlled.

According to the present invention, a method and an apparatus is provided which allows air containing the fumes to be removed to the exterior or removed on a filter device before the cleaner air is being recycled.

Also, it should be understood, that the air drawn into the interior space in addition to be temperature controlled by heating or cooling, also may be added humidity by spraying water droplets or using a filter device, or added other components, like nitrogen gas, carbon dioxide or inert gasses to control the environment in the hood.

In one preferred embodiment, the inlet air is drawn through a humid filter device to ensure high and uniform humidity in the chamber.

In another preferred embodiment, the humidity is controlled by spraying water droplets or having a water surface.

In yet another preferred embodiment, recycled air is drawn through filters to remove fumes and filters to adjust the humidity.

In yet another preferred embodiment, the humidity is controlled to never be below a predetermined level, to prevent drying out of the sample.

Also, disfectantes, UV protectants or other compounds could be added to the inlet air to prevent microbial growth or discolouring.

It should be understood that by controlling the environment by the present invention, the mechanical and electrical parts are also protected from corrosion and wear. Also, by an apparatus according to the invention the air may be moved around inside the interior space which ensures uniform and controllable temperature control.

BRIEF DESCRIPTION OF THE DRAWINGS

The invention is described with reference to a preferred embodiment with reference to the drawings, in which.

BEST MODES FOR CARRYING OUT THE INVENTION

A staining apparatus 1 according to the invention is shown in the figures. The staining apparatus 1 comprises a rectangular housing frame 4 surrounding a reagent station 2 comprising an array of reagent bottle compartments wherein each compartment a reagent vial 3 is placed, and a first and second slide sections 5 wherein a number of separate rack assemblies 11 is placed, potentially in some embodiments in one or more drawer assemblies 6, and where each rack assembly 11 accommodates a number of microscope slides 7 mounted side by side in the rack assembly. In the embodiment shown, each rack may hold up to 8 slides, but the rack may be designed to hold any suitable number of slides. With eight racks arranged side by side, the shown embodiments may hold up to 64 slides 7 each having a biological sample, e.g. a tissue mounted on the upper side of the slide, so that reagent may be applied from above to the sample on each slide.

Multiple drawers 6 allow for one or a plurality of sample processing protocols to be performed by the system. Past efforts at sample processing, as previously described, may have been limited to processing sequences for an entire batch of carriers within the system. The present invention, however, in part by providing a plurality of drawers 6 and carrier rack assemblies 11, may allow for multiple batch processing, including real-time or adaptive capabilities for multiple batch processing, as further described below.

Indicator elements may be provided to indicate a status of the drawers 6 and the carriers or materials within each drawer for an operator of the system. In one embodiment, visual indicators, such as light emitting diodes in preferred embodiments, indicate if a drawer is available during operation of the sample processing system, and may indicate conditions such as a locked or open condition of a corresponding drawer, 6 carrier capacity status of the drawer or of a carrier rack assembly 11 within the drawer 6, and chemical status of the sample processing system, such as reagent loading status or capacity. A warning indication may be given by the indicator elements, as well as other indicative signals. One or a plurality of sensors may be utilized to determine the status of the drawer as indicated by the indicator elements and to further provide processing status as further described below. Furthermore, adaptive scheduling of sample and slide insertion and removal into the system may be accommodated on an ongoing basis throughout operation of the sample processing system.

Figure 1:
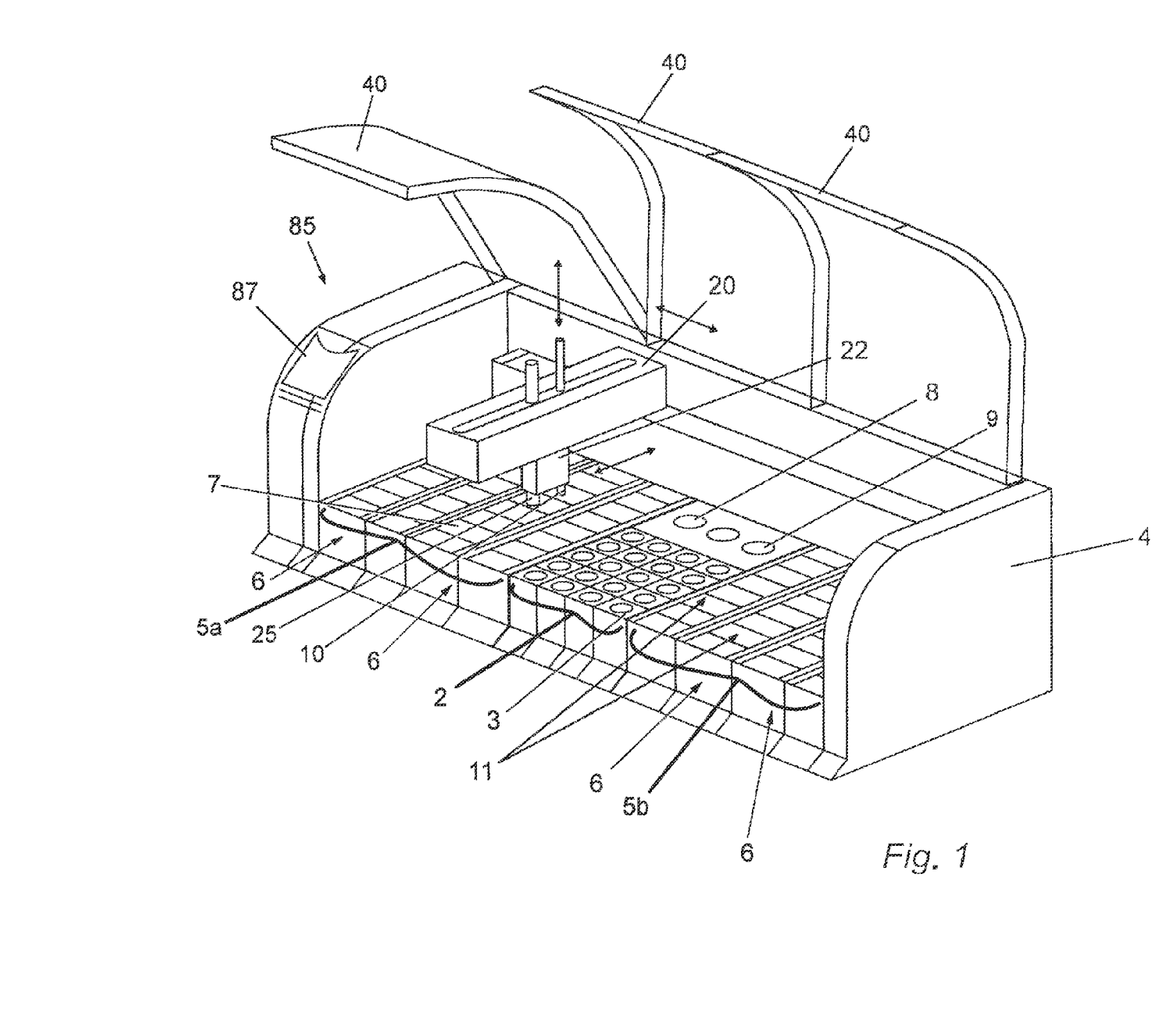
FIG. 1 is a schematic perspective view of a staining apparatus according to the preferred embodiment of the invention.
Figure 2:
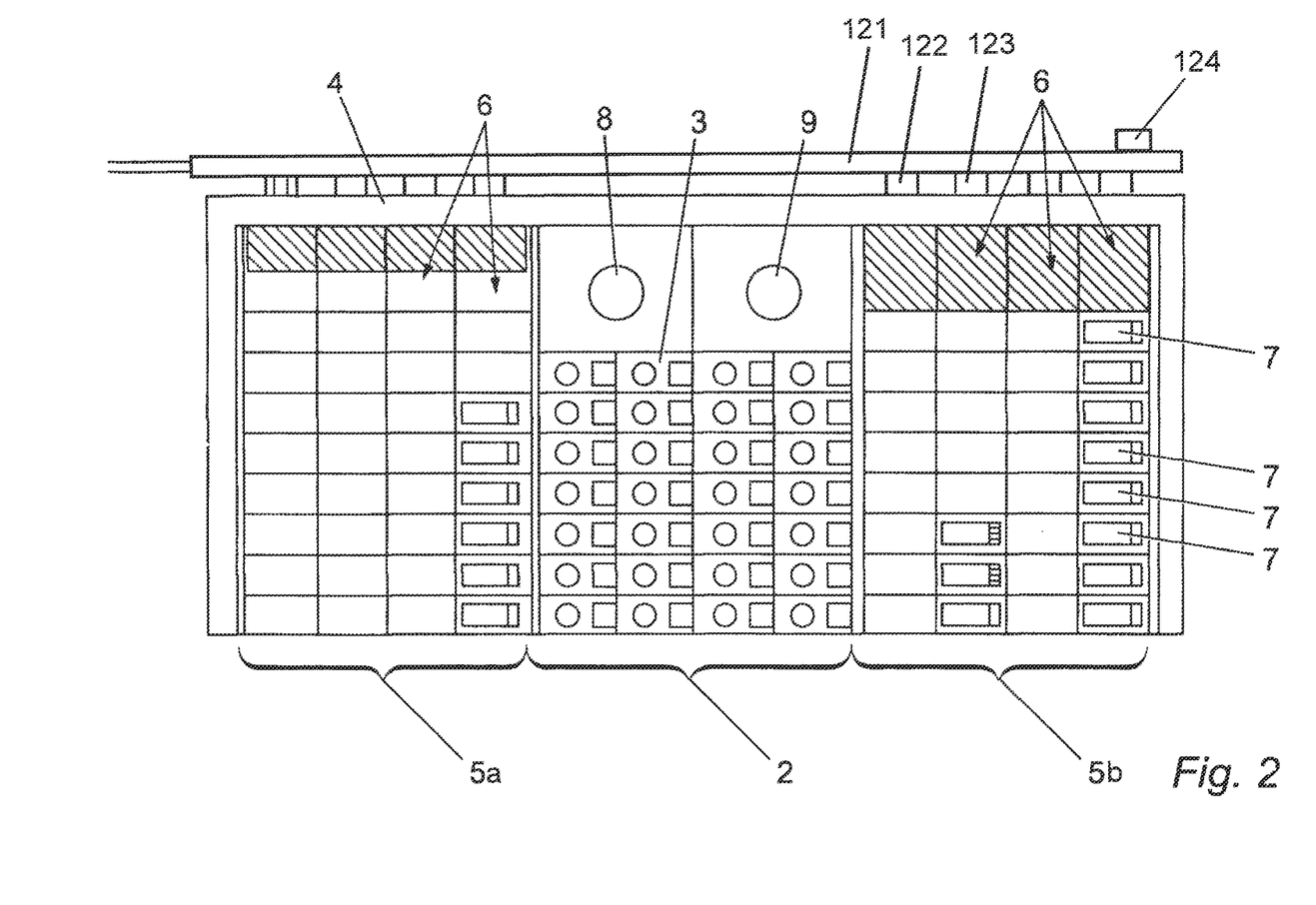
FIG. 2 is a top view of the work area in the staining apparatus shown in FIG. 1.

A sensor may be provided in some embodiments that may automatically identify information from one or more slides 7. In some embodiments, protocol information may be provided by an adaptive sample processing control system. The sample processing system may process one or more slides 7, or one or more batches of slides 7, concurrently, sequentially, or in any other temporal fashion, potentially in accordance with protocol information provided by a slide having a sample or provided by the adaptive sample processing control system. Sample batches or individual slides 7 may be inserted or removed during processing protocol steps by the control and monitoring accomplished by the adaptive sample processing control system In some embodiments, the system may comprise independent and redundant slide staining modules, such as drawer assemblies 6. Throughput is based on time to first result with the system allowing access to completed slides 7 as soon as a staining module has completed the scheduled staining tasks. The multiple independent and redundant staining modules allow for both continuous and batch processing of slides 7. Additionally, each independent staining module also allows for the independent pre-treatment and staining of each slide. A carrier rack assembly 11 may be used to introduce slides 7 to be processed into the drawer 6, the drawer, carrier rack assembly 11, and components thereof forming a stain module. The slides 7 may occupy one or more positions of the carrier rack assembly 11, such as at carrier retention devices, up to the capacity of the carrier rack assembly 11 with the potential for each slide being processed independently of other slides 7 configured with carrier rack assembly 11. Embodiments of the stain modules, drawers, rack assemblies, and components thereof are also shown in FIG. 1. FIG. 1 also provides other embodiments of system features, such as an embodiment of the arm 20 and the component features of the arm.

Carrier rack assemblies 11 having one or more slides 7 may be introduced into the staining modules by introduction into drawers 6 one at a time or in any combination until all staining modules are occupied. There may be no restrictions as to the order, number or timing of when the carrier rack assemblies 11 are introduced into the system, the system allowing for adaptive scheduling of sample loading. Staining modules, and in some embodiments the drawers 6 of the staining modules, will lock out access to the slides 7 during the processing period and may release them to the operator upon completion of the staining process on the last slide. In some embodiments, the order in which the carrier rack assemblies 11 are released is dependant on the time required to process the last slide of the rack assembly. Slides 7 may be processed in the most time efficient manner independently of the order to which they were introduced into the system.

A robot arm 20 for moving a probe 10 in X and Y (as well as Z) direction as indicated by the arrows X and Y is arranged above the frame 4 of the staining apparatus. The robot arm 20 may is therefore position the probe 10 above all reagent vials 3 as well as above all the microscope slides 7, and may further operate the probe 10 to aspirate portions of reagent contained in any of the vials 3, to transfer the portion of reagent and apply it to any of the slides 7 in order to provide a selected staining or treatment of the sample on each slide 7. By use of suitable control, e.g. a computer (not shown) having the appropriate software and input data for the purpose, this staining apparatus 1 is able to automatically stain or treat samples requiring different staining or treatment reagents and processes.

As shown in FIG. 1, the probe 10 is accommodated in a robotic head 22 and is manipulated by the robot arm 20. The probe 10 is raised to an upper position (in a Z direction) where it is clear of the vials 3 underneath the probe 10, but the robot comprises means in the robotic head 22 for lowering the probe 10 in order to dip the probe tip into the content of a selected reagent vial 3 and to aspirate a selected amount of reagent for the selected staining or treatment process. The robotic head 22 may also be provided with a CCD camera 25, in some embodiments configured to point downwards. The camera is utilised to determine status information of the slides and the reagent bottles and other features of the apparatus in the work area, for example reading information which may or may not be encrypted, that is provided on a reagent container to determine the reagent type and the reagent location within the system. The camera may also determine status of the tissue sample carriers, for example the location of a particular slide, informational indicia, such as which may be converted into an encrypted format, that indicate information about the tissue sample presented on the slide or the processing protocol to be performed.

The staining apparatus 1 of the present embodiment further comprises a probe washing station 8 and a reagent mixer 9, and the robot arm 20 is furthermore arranged to transfer the probe 10 to the washing station 8 as well as to the reagent mixer 9.

Figure 3:
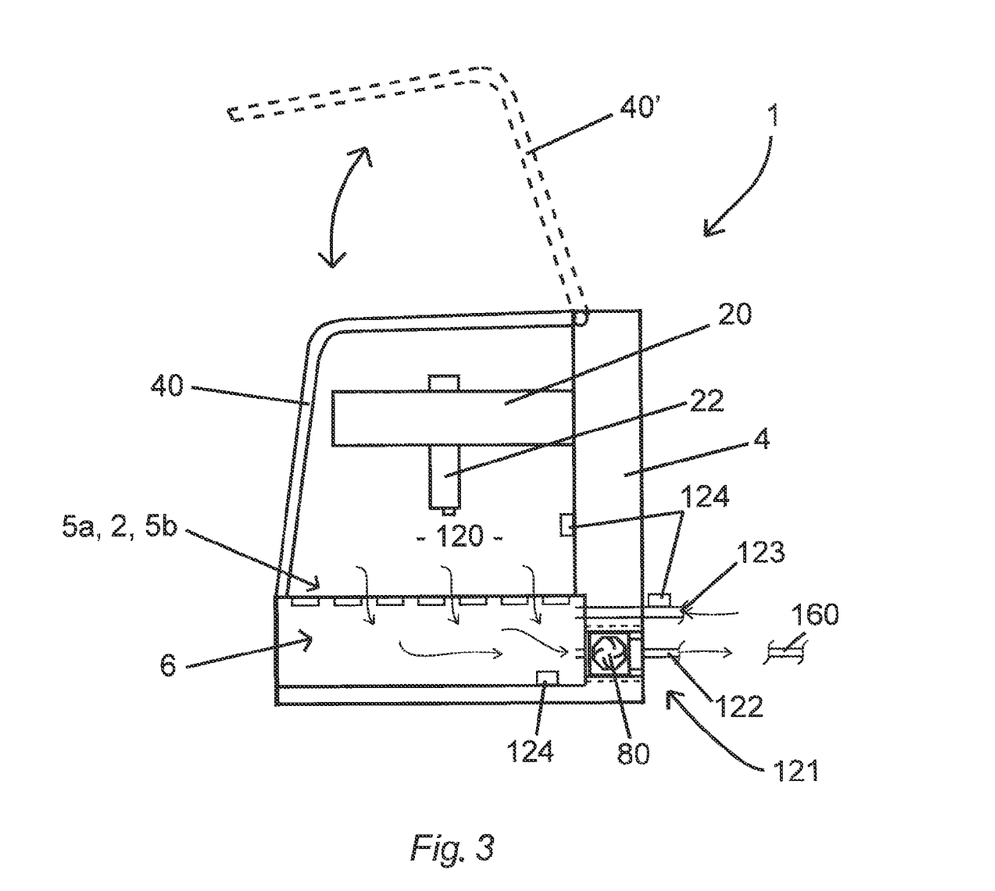
FIG. 3 is a schematic side view of the staining apparatus of FIG. 1.

As shown in FIG. 3, the apparatus 1 is provided with an openable hood cover 40, which is pivotably attached to the frame housing 4. The hood 40 is shown in a closed position and an open position 40' is indicated in dotted lines in the figure.

In the bottom of the frame housing 4, the slide rack assemblies 11, potentially in some embodiments in one or more drawer assemblies 6 are provided. An interior space 120 is defined by this hood cover 40 and the frame 4. The staining sections 5 and the reagent station 2 are arranged such that they are accessible by the robotic arm 20 via the equipment arranged on the robotic head 22.

A climate control device 121 is provided for controlling the pressure and potentially also the temperature and the humidity of the air in the interior space 120 inside the apparatus 1. This climate control 121 includes an outlet 122 and an inlet 123 allowing for an exchange of air in a controlled manner. Exhausted air from the interior space may be directed to a collection storage or disposed of in other manners depending on the requirements on the location of the apparatus. The exhausted air may—in particular in some staining or other processes—include volatile fumes or other toxic or unwanted fumes from the reagents and other liquids used for the processing of the biological samples.

The ambient air in the interior space 120 is drawn through the rack assembly 11 of the drawer assembly 6 in the staining sections 5. In the drawer assembly 6, other processing devices are preferably also provided, such as pretreatment tanks in which the biological specimens arranged on slides may be immersed in a pretreatment liquid which is often heated to a processing temperature. By drawing the fumes out of the interior space 120 at a location close to the heating sources and below the level in which the slides are arranged, the fumes are essentially prevented from diffuse to widely in the interior space, whereby the risk of such fumes coming into unwanted contact with biological samples, other reagents or processing liquids may be avoided.

Besides maintaining a slight sub-pressure inside the hood, the climate control may also be adapted to controlling the temperature and the humidity inside the apparatus, so that such climatic conditions do not interfere with the staining processes. Hereby, the apparatus may easily be adapted to changes in the environment, such as seasonal changes, temperature changes, just as the apparatus according to the invention may be able to adapt itself to a specific location, e.g. adapt to difference in altitude, etc.

The temperature, humidity, airflow rate and/or other environmental factors can be controlled by a feed back mechanism from a sensor device, such as one or more sensors 125 arranged in the hood or elsewhere inside the interior space and/or external sensors 125, which may be advantageous in order to compensate for external influences such as high temperature or extremely dry climate in local areas having extreme climate variations.

The system may further have the ability to vent toxic and or flammable fumes from inside the cabinet portions or enclosure to exit ports that can be connected to an external system vent or hood, such as vent 160. Embodiments may comprise exit ports from the internal enclosure of the system and exit ports from the bulk fluid containers of the system, such as reagent containers. Fumes may be isolated and removed from various compartments within the system. An environmental control system addresses the system's ventilation to ensure the evacuation of volatile organic vapours, keeping the concentration of these materials below established toxic and explosive limits.

Figure 4:
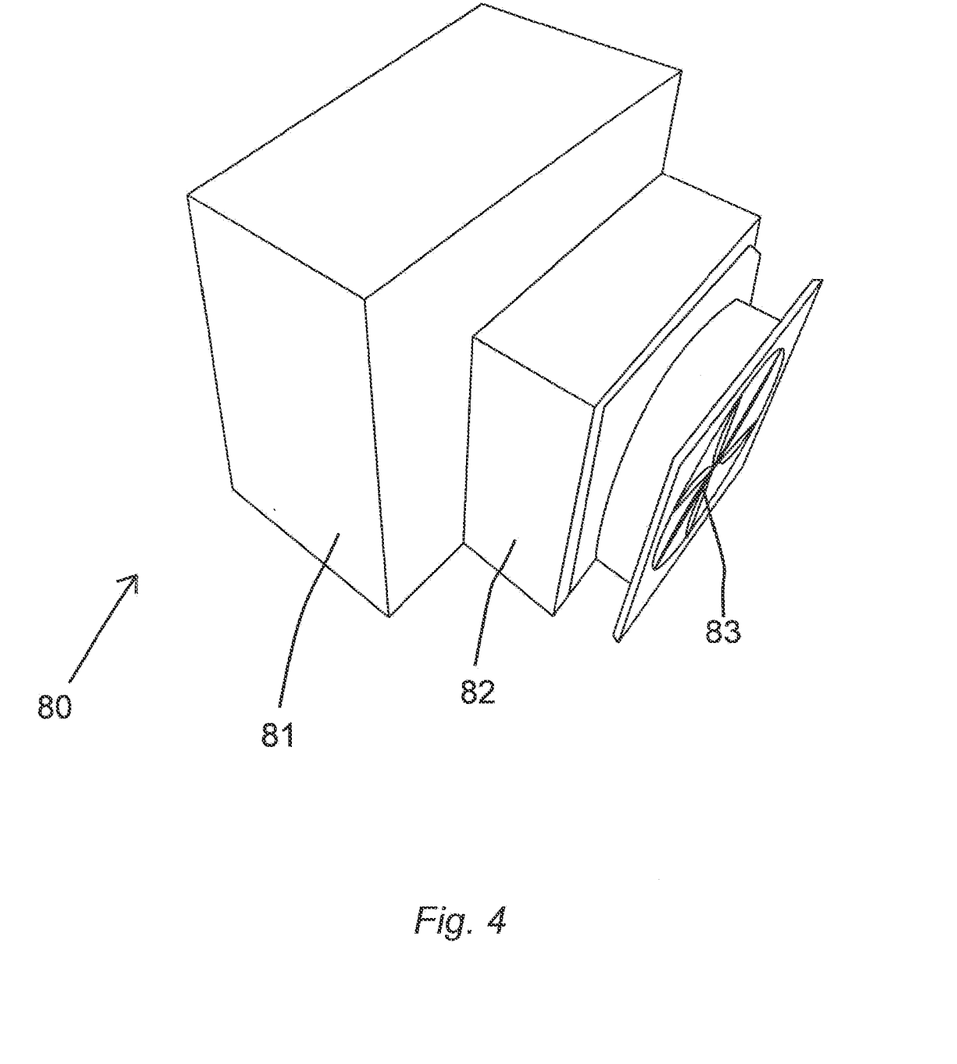
FIG. 4 is an example of a ventilation assembly mountable in the housing in an apparatus according to the invention.

In some embodiments, a ventilation system such as that shown in FIGS. 3 and 4 will draw hazardous fumes from the vicinity of each processing tank in the drawer assemblies 6 by an exhaustion device that may comprise dedicated ducts 122, 123. These ducts will feed a manifold 121 running along the rear of the instrument. The ventilation system may further comprise a fan in an air inlet opening in the housing frame 4 through which air may be exchanged. A separate ventilation system for an electronic chassis of the system may be similarly isolated having independent air input and output vents. Each of these systems has independent air input and output air vents. At one end of the manifold, a centrifugal blower will exhaust the fumes to an exit port that may be connected to the facility hood/exhaust system.

In FIG. 4, a ventilation assembly 80 for mounting in the apparatus is shown. Through this ventilation assembly 80 air may be exchanged between the interior space 120 and the surroundings. In addition to the inlet and outlet ducts 122, 123, air manipulation devices 81, 82 may be arranged. These air manipulation devices may include moisture control, air pressure and air flow regulation in order to control the environment in the interior space automatically in response to sensor 125 readings inside the interior space.

Above, the apparatus according to the invention is described according to some preferred explanatory embodiments. However, it is realised by the invention that many other variations and equivalents of the apparatus may be carried out without departing from the scope of the invention as specified in the accompanying claims.

As can be easily understood from the foregoing, the basic concepts of the present invention may be embodied in a variety of ways. It involves both sample processing techniques as well as various systems, assemblies, and devices to accomplish sample processing, input, and other functions. In this application, the sample processing techniques are also disclosed as part of the results shown to be achieved by the various systems, assemblies, and devices described and as steps which are inherent to utilization. They should be understood to be the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included in this application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in device-oriented terminology, each element of the device implicitly performs a function. Importantly, neither the description nor the terminology is intended to limit the scope of the claims which may be included at any time.

It should also be understood that a variety of changes may be made without departing from the essence of the invention. Such changes are also implicitly included in the description. They still fall within the scope of this invention. A broad disclosure encompassing both the explicit embodiment(s) shown, the great variety of implicit alternative embodiments, and the broad methods or processes and the like are encompassed by this disclosure and may be relied upon at any time.

Further, each of the various elements of the invention and claims may also be achieved in a variety of manners. This disclosure should be understood to encompass each such variation, be it a variation of an embodiment of any apparatus embodiment, a method or process embodiment or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "retention element" should be understood to encompass disclosure of the act of "retaining"—whether explicitly discussed or not—and, conversely, were there effectively disclosure of the act of "retaining", such a disclosure should be understood to encompass disclosure of a "retention element" and even a "means for retaining". It should also be understood that in jurisdictions where specific language may be construed as limiting, as but one example in the United States where some interpretations of "means for" elements can be construed narrowly, broader equivalent language may be used and should be understood as encompassed by this specification. Such changes and alternative terms are to be understood to be explicitly included in the description.

Any patents, patent applications, publications, or other references mentioned in this application for patent are hereby incorporated by reference. In addition, as to each term used it should be understood that unless its utilization in this application is inconsistent with such interpretation, common dictionary definitions should be understood as incorporated for each term and all definitions, alternative terms, and synonyms such as contained in the Random House Webster's Unabridged Dictionary, second edition are hereby incorporated by reference as well as the definitions presented by searchStorage.com, such to be considered as representing the meaning of the terms as understood by computer professionals. Finally, any priority case for this application is hereby appended and hereby incorporated by reference.

Thus, the applicant(s) should be understood to have support to claim at least i) each of the sample processing systems and subsystems as herein disclosed and described, ii) the related methods disclosed and described, iii) similar, equivalent, and even implicit variations of each of these systems, assemblies, devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, and ix) methods and systems, assemblies, devices, and apparatuses substantially as described hereinbefore and with reference to any of the accompanying examples, x) the various combinations and permutations of each of the elements disclosed, xi) each potentially dependent claim or concept as a dependency on each and every one of the independent claims or concepts presented, xii) processes performed with the aid of or on a computer as described throughout the above discussion, xiii) a programmable system as described throughout the above discussion, xiv) a computer readable memory encoded with data to direct a computer comprising means or elements which function as described throughout the above discussion, xv) a computer configured as herein disclosed and described, xvi) individual or combined subroutines and programs as herein disclosed and described, xvii) the related methods disclosed and described, xviii) similar, equivalent, and even implicit variations of each of these systems and methods, xix) those alternative designs which accomplish each of the functions shown as are disclosed and described, xx) those alternative designs and methods which accomplish each of the functions shown as are implicit to accomplish that which is disclosed and described, xxi) each feature, component, and step shown as separate and independent inventions, and xxii) the various combinations and permutations of each of the above.

Further, if or when used, the use of the transitional phrase "comprising" or the like is used to maintain the "open-end" claims herein, according to traditional claim interpretation. Thus, unless the context requires otherwise, it should be understood that the term "comprise" or variations such as "comprises" or "comprising" or the like, are intended to imply the inclusion of a stated element or step or group of elements or steps but not the exclusion of any other element or step or group of elements or steps. Such terms should be interpreted in their most expansive form so as to afford the applicant the broadest coverage legally permissible.

Any claims set forth at any time are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

What is claimed is:

1. An apparatus for automatic processing of at least one biological sample accommodated on at least one carrier member, comprising:
    a housing frame;
    a plurality of carrier members;
    a plurality of carrier racks within the housing, each of the carrier rack being configured for supporting at least one of the plurality of carrier members;
    a robotic reagent dispensing head within the housing that performs ongoing robotic processing, including dispensing of reagents;
    at least one sample processing section within the housing for accommodating at least one of the plurality of carrier racks;
    a cover for protecting said at least one sample processing section in said housing, said cover enclosing the sample processing section and defining an interior space between the housing and the cover;
    at least one climate control device for controlling the environment within said interior space defined by the cover;
    a sensor device for providing feedback signals to the climate control device; and
    a data processing device configured to control the at least one climate control device, wherein the data processing device comprises a processing protocol including instructions to apply a predetermined amount of reagents in a predetermined sequence on a first carrier member of the plurality of carrier members,
    wherein a first carrier rack is configured to permit the first carrier member supported by the first carrier rack, for which the processing is completed, to be removed from the apparatus without opening the cover or interrupting the dispensing of reagents with the robotic reagent dispensing head, and
    wherein a second carrier rack is configured to permit a second carrier member supported by the second carrier rack to be inserted into the apparatus without opening the cover or interrupting the dispensing of reagents onto the first carrier member, supported by the first carrier rack, with the robotic reagent dispensing head.

2. An apparatus according to claim 1, wherein the sensor device is adapted to sense at least one climate parameter from the group consisting of temperature, pressure, humidity, airspeed and the presence of toxic elements in fume.

3. An apparatus according to claim 1, further comprising an air inlet/outlet manifold, wherein the sensor device comprises external sensors located at or inside the air inlet/outlet manifold, in a laboratory facility accommodating the apparatus, or outside a building accommodating the laboratory.

4. An apparatus according to claim 1, wherein the cover comprises a plurality of covers arranged to cover a plurality of sections of the apparatus, wherein the plurality of sections includes the at least one sample processing section.

5. An apparatus according to claim 4, wherein a plurality of interior spaces of the apparatus is defined by said plurality of covers, each interior space being defined as the volume located between the cover and the housing, and each interior space including at least one section comprising at least one sample on the first carrier member and/or at least one section comprising at least one reagent in a container.

6. An apparatus according to claim 5, wherein the at least one climate control device controls the climate of the at least one biological sample on the first carrier member in each interior space according to the processing protocol defined for that particular sample.

7. An apparatus according to claim 6, wherein the sensor device comprises internal sensors and external sensors, and wherein the at least one climate control device receives input signals from the internal and/or external sensors and controls the climate in each interior space according to the input signals.

8. An apparatus according to claim 1, wherein the climate control device comprises a ventilation system with an exhaustion device having a plurality of ducts for exchanging the air in the interior space with a manifold in the housing frame.

9. An apparatus according to claim 8, wherein the ventilation system comprises a centrifugal blower in an air inlet opening in the manifold of the housing frame through which air may be exchanged.

10. An apparatus according to claim 9, further comprising at least one air manipulation device with the air inlet opening for adapting the air temperature, pressure, air flow rate, and humidity of the inflowing air into the apparatus.

11. An apparatus according to claim 1, wherein the climate control device comprises an exhaustion device with an outlet for removing fumes from the interior space.

12. An apparatus according to claim 11, wherein the climate control device is a device for recycling air for humidity, temperature, and toxic control, a device for removing toxic elements from the air to be recycled, a device for supplying humidity to the air to be recycled, or a heater/cooling device for controlling the temperature of the air to be recycled.

13. An apparatus according to claim 1, wherein the housing frame comprises at least one air inlet opening adapted to supply air into the interior space, and wherein the climate control device comprises an air manipulation device configured to adapt the inflowing air with predetermined characteristics, the air manipulation device being provided in the at least one air inlet opening.

14. An apparatus according to claim 13, wherein said air manipulation device comprises a humid filter device adapted to draw inflowing air through the humid filter device and provide high and uniform humidity in the chamber.

15. An apparatus according to claim 14, wherein the air manipulation device sprays water droplets or has a water surface and thereby controls humidity.

16. An apparatus according to claim 1, wherein the sensor device registers one or more parameters of the air in interior space of the apparatus, said sensor device being arranged in a vicinity of the cover and/or in a vicinity of the at least one carrier member on the carrier rack.

17. An apparatus for automatic processing of at least one biological sample accommodated on at least one carrier member, comprising:
    a housing frame;
    a plurality of reagent containers;
    a plurality of container racks within the housing, each of the container rack being configured for supporting at least one of the plurality of reagent containers;
    a robotic reagent dispensing head within the housing that performs ongoing robotic processing, including dispensing of reagents obtained from the plurality of reagent containers;

at least one sample processing section within the housing accommodating the at least one biological sample;

at least one reagent section within the housing accommodating at least one of the plurality of carrier racks;

a cover for protecting said at least one sample processing section and said at least one reagent section in said housing, said cover enclosing the sample processing section and the reagent section and defining an interior space between the housing and the cover; at least one climate control device for controlling the environment within said interior space defined by the cover;

a sensor device for providing feedback signals to the climate control device; and a data processing device configured to control the at least one climate control device, wherein the data processing device comprises a processing protocol including instructions to apply a predetermined amount of reagents in a predetermined sequence to the at least one biological sample, wherein a first container rack is configured to permit a first reagent container supported by the first container rack, to be removed from the apparatus without opening the cover or interrupting the dispensing of reagents with the robotic reagent dispensing head, and wherein a second container rack is configured to permit a second reagent container supported by the second container rack to be inserted into the apparatus without opening the cover or interrupting the dispensing of reagents with the robotic reagent dispensing head.

18. An apparatus according to claim 17, wherein the sensor device is adapted to sense at least one climate parameter from the group consisting of temperature, pressure, humidity, airspeed and the presence of toxic elements in fume.

19. An apparatus according to claim 17, further comprising an air inlet/outlet manifold, wherein the sensor device comprises external sensors located at or inside the air inlet/outlet manifold, in a laboratory facility accommodating the apparatus, or outside a building accommodating the laboratory.

20. An apparatus according to claim 17, wherein the cover comprises a plurality of covers arranged to cover a plurality of sections of the apparatus, wherein the plurality of sections includes the at least one sample processing section.

21. An apparatus according to claim 20, wherein a plurality of interior spaces of the apparatus is defined by said plurality of covers, each interior space being defined as the volume located between the cover and the housing, and each interior space including at least one section comprising at least one sample on the at least one carrier member and/or at least one section comprising at least one of the plurality of reagent containers.

22. An apparatus according to claim 21, wherein the at least one climate control device controls the climate of the at least one biological sample on the at least one carrier member in each interior space according to the processing protocol defined for that particular sample.

23. An apparatus according to claim 22, wherein the sensor device comprises internal sensors and external sensors, and wherein the at least one climate control device receives input signals from the internal and/or external sensors and controls the climate in each interior space according to the input signals.

24. An apparatus according to claim 17, wherein the climate control device comprises a ventilation system with an exhaustion device having a plurality of ducts for exchanging the air in the interior space with a manifold in the housing frame.

25. An apparatus according to claim 24, wherein the ventilation system comprises a centrifugal blower in an air inlet opening in the manifold of the housing frame through which air may be exchanged.

26. An apparatus according to claim 25, further comprising at least one air manipulation device with the air inlet opening for adapting the air temperature, pressure, air flow rate, and humidity of the inflowing air into the apparatus.

27. An apparatus according to claim 17, wherein the climate control device comprises an exhaustion device with an outlet for removing fumes from the interior space.

28. An apparatus according to claim 27, wherein the climate control device is a device for recycling air for humidity, temperature, and toxic control, a device for removing toxic elements from the air to be recycled, a device for supplying humidity to the air to be recycled, or a heater/cooling device for controlling the temperature of the air to be recycled.

29. An apparatus according to claim 17, wherein the housing frame comprises at least one air inlet opening adapted to supply air into the interior space, and wherein the climate control device comprises an air manipulation device configured to adapt the inflowing air with predetermined characteristics, the air manipulation device being provided in the at least one air inlet opening.

30. An apparatus according to claim 29, wherein said air manipulation device comprises a humid filter device adapted to draw inflowing air through the humid filter device and provide high and uniform humidity in the chamber.

31. An apparatus according to claim 29, wherein the air manipulation device sprays water droplets or has a water surface and thereby controls humidity.

32. An apparatus according to claim 17, wherein the sensor device registers one or more parameters of the air in interior space of the apparatus, said sensor device being arranged in a vicinity of the cover and/or in a vicinity of the at least one carrier member on the carrier rack.

* * * * *